United States Patent [19]
Doná

[11] Patent Number: 4,686,181
[45] Date of Patent: Aug. 11, 1987

[54] SPECIFIC BINDING ASSAY EMPLOYING ANTI-G6PDH AS LABEL

[75] Inventor: Valerio Doná, Via Gramsci, Italy

[73] Assignee: Miles Laboratories, Inc., Elkhart, Ind.

[21] Appl. No.: 673,152

[22] Filed: Nov. 19, 1984

[30] Foreign Application Priority Data

Mar. 9, 1984 [IT] Italy ............................. 47834 A/84

[51] Int. Cl.⁴ .................... G01N 33/53; C12Q 1/32; C12N 9/04
[52] U.S. Cl. ........................................ 435/7; 435/26; 435/190; 435/810
[58] Field of Search ........................... 435/7, 26, 190; 436/512, 825, 537

[56] References Cited

U.S. PATENT DOCUMENTS 4,341,866  7/1982  Yoshida ................................ 435/7

OTHER PUBLICATIONS

Maggio et al., *Enzyme Immunoassay*, Chap. 5: "Principles of Homogeneous Enzyme-Immunoassay", pp. 106-110; 124-127, CRC Press, Florida (1980).

Ngo et al., *FEBS Letters;* vol. 116, No. 2, Jul. 1980, pp. 285-288.

*Primary Examiner*—Christine M. Nucker
*Attorney, Agent, or Firm*—Andrew L. Klawitter

[57] ABSTRACT

A specific binding assay method and reagent system based on the use of an inhibitory anti-enzyme, e.g., antibody or fragment thereof, as the label component. Such method and reagent system have been improved by selection of anti-(glucose-6-phosphate dehydrogenase) [anti-G6PDH] as the anti-enzyme label. The improved label is monitored by its ability to inhibit G6PDH. The resulting assay is more sensitive, requires lesser quantities of reagents, is less susceptible to sample interferences, and employs a reagent system having greater stability than the published prior art method employing an anti-peroxidase label. The present invention is particularly applicable to homogeneous immunoassays for determining substances appearing at low concentrations in biological fluids such as urine and serum.

17 Claims, 8 Drawing Figures

SPECIFIC BINDING ASSAY EMPLOYING ANTI-G6PDH AS LABEL

BACKGROUND OF THE INVENTION

1. Field Of The Invention

The development of specific binding assay techniques has provided extremely useful analytical methods for determining various organic substances of diagnostic, medical, environmental and industrial importance which appear in liquid mediums at very low concentrations. Specific binding assays are based on the specific interaction between the substance under determination herein referred to as the "analyte", and a binding counterpart thereof. Where one of the analyte and its binding counterpart is an antibody and the other is a corresponding hapten or antigen, the assay is known as an immunoassay.

In conventional specific binding assay techniques, a sample of the liquid medium to be assayed is combined with reagent systems of various compositions. Such compositions include a labeled conjugate comprising a binding component incorporated with a label. The binding component in the labeled conjugate interacts with other constitutents, if any, of the reagent system and the analyte in the medium under assay to form two species or forms of the labeled conjugate, a bound-species and a free-species. In the bound-species, the binding component, e.g., a hapten or antigen, in the labeled conjugate is bound by a corresponding binding counterpart, e.g., an antibody, whereas in the free-species, the binding component is not so bound. The relative amount or proportion of the labeled conjugate that results in the bound-species compared to the free-species is a function of the presence or amount of the analyte in the test sample.

Where the labeled conjugate in the bound-species is essentially indistinguishable in the presence of the labeled conjugate in the free-species by the means used to monitor the label, the bound-species and the free-species must be physically separated in order to complete the assay. This type of assay is referred to in the art as "heterogeneous". Where the bound-species and free-species forms of the labeled conjugate can be distinguished in the presence of each other, a "homogeneous" format can be followed and the separation step avoided.

This invention relates to specific binding assay methods and reagent systems for the quantitative or qualitative determination of an analyte in a liquid medium. In particular, the present invention relates to such methods and systems, especially of the homogeneous type, wherein the label employed is an antienzyme, e.g., an inhibitory antibody, or fragment thereof, for an enzyme.

2. Description Of The Prior Art

The first highly sensitive specific binding assay to be discovered was the radioimmunoassay which employs a radioactive isotope as the label. Such an assay necessarily must follow the heterogeneous format since the monitorable character of the label is the same in the free- and bound-species. Because of the inconvenience and difficulty of handling radioactive materials and the necessity of a separation step, homogeneous assay systems have been devised using materials other than radioisotopes as the label component, including enzymes, bacteriophages, metals and organometallic complexes, coenzymes, enzyme substrates, enzyme modulators, e.g., activators and inhibitors, cycling reactants, spin radicals, organic and inorganic catalysts, prosthetic groups, chemiluminescent reactants, and fluorescent molecules.

Generally representative of such homogeneous specific binding assays are those described in the following references: U.S. Pat. Nos. 4,134,792; 4,226,978; 4,230,797; 4,238,195; 4,238,565; 3,935,074; 4,208,479; 4,233,401; 4,256,834; 3,817,837; 4,043,872; 3,996,345; 4,233,402; 4,160,645; 3,690,834; and 4,278,866; and British Pat. Specification No. 1,595,101. Of these techniques, the following involve, in some fashion, label monitoring reactions based in modulation of enzyme activity by anti-enzyme.

U.S. Pat. Nos. 4,134,792 and 4,278,866 and British Pat. Specification No. 1,595,101 describe specific binding assays employing an enzyme modulator as the label. When performed in the homogeneous mode, the modulation effect of the labeled conjugate on the enzyme, in most cases an inhibition of enzyme activity, is altered, usually decreased, in the bound-species.

U.S. Pat. Nos. 4,208,479 and 4,233,401 describe homogeneous specific binding assays wherein an enzyme is employed as the label. A labeled conjugate is constructed such that the catalytic activity of the labeling enzyme is substantially retained; however, upon binding of the binding counterpart, e.g., antibody to the labeled conjugate, enzymatic activity is diminished.

The use of anti-enzyme labels in specific binding assays, particularly of the homogeneous type, is described in U.S. patent application Ser. No. 285,605, filed July 21, 1981, and assigned to Miles Laboratories, Inc., Elkhart, Ind., USA, the parent company of the present assignee. Such patent application describes the use of antibodies to a variety of different enzymes as labels in specific binding assays and provides a particular example wherein anti-peroxidase is used as the label. The use of anti-peroxidase labels is also described by a former co-worker with the inventor U.S. of Ser. No. 285,605 in *FEBS Letters* 116(2): 285-288 (July 1980)-Ngo and Lenhoff.

SUMMARY OF THE INVENTION

The present invention provides a distinct improvement in anti-enzyme labeled specific binding assay methods and reagent systems by the selection of glucose-6-phosphate dehydrogenase (G6PDH) as the enzyme inhibitable by the anti-enzyme (anti-G6PDH) label. The progress of the assay is monitorable by measuring the extent of inhibition of G6PDH by the anti-G6PDH label. The anti-G6PDH label is preferably a whole antibody, or a fragment thereof, of the conventional polyclonal or monoclonal variety. The assay can be of the heterogeneous or homogeneous type, with the latter being particularly advantageous. A wide variety of analytes can be determined from low molecular weight haptens such as drugs, hormones, and metabolites, to high molecular weight antigens such as proteins and polypeptides. The method is applicable to use in a variety of formats, from liquid test systems to solid state test devices, and from manual to automated systems.

The present improvement provides particular advantages over the prior art anti-enzyme labeled binding assays, especially the anti-peroxidase labeled assay, such as described by Ngo and Lenhoff, supra. Anti-G6PDH labeled conjugates have been found to be capable of inhibiting 100% of the enzymatic activity of the monitoring enzyme, G6PDH, whereas the best published results for the peroxidase/anti-peroxidase system show the capability of that system to give only about 75% inhibition. This significantly increased inhibitory capacity of the present anti-G6PDH label results in a more sensitive assay and an assay requiring significantly lesser quantities of reagents, particularly the synthetically prepared labeled conjugate. Moreover, the G6PDH/anti-G6PDH system of the present invention has been found to be significantly less susceptible to sample interferences and to be significantly more stable as a reagent system than the prior art peroxidase-based method. It is particuarly preferred to employ G6PDH obtained from the microbial source *Leuconostoc mesenteriodes* (EC 1.1.1.49) since such form of the enzyme can use nicotinamide adenine dinucleotide (NAD) as cofactor, whereas G6PDH which is endogeneous to mammalian body fluids, e.g., human urine and serum samples, requires a different cofactor, nicotinamide adenine dinucleotide phosphate (NADP), for activity. On the other hand, peroxidative activity exists at significant levels in biological fluids of analytical interest. Furthermore, as an assay reagent, peroxidase is known to be relatively unstable at the low concentrations required for its use in immunoassays.

The present improved assay can be performed in a manner which provides a highly sensitive assay, i.e., capable of detecting less than 1 nanomolar (nM; $10^{-9}$ molar) analyte following a competitive binding, homogeneous format. Such sensitivity is the result of selecting a colorimetric end-point protocol with incubation times in the range of 60 minutes for the competitive binding reaction and 20 minutes for the enzymatic monitoring reaction. Chromogenic indicators can be selected which have absorbances at longer wavelengths than typical absorbances due to constituents of biological fluids. Additional sensitivity is possible by using fluorogenic indicators.

The present method for determining an analyte in a test sample involves combining or contacting the test sample with assay reagents which include a labeled conjugate having anti-G6PDH as a label component, such anti-G6PDH label being capable of measurably inhibiting the catalytic activity of G6PDH. The identity of the binding component to which the anti-G6PDH label is linked and the further binding elements, if any, of the assay reagents are selected, as is known in the art, according to the desired assay protocol. For instance, following a competitive binding format, the binding component in the labeled conjugate will be the analyte or an analog thereof and the assay reagents would additionally include a binding counterpart, such as an antibody, for the analyte.

The net result of the combination of the test sample with the assay reagents is the formation of a reaction mixture having a bound-species and a free-species of the labeled conjugate. The assay is completed by determining by the extent of inhibition of G6PDH by the labeled conjugate in the bound-species or the free-species. Measurement of G6PDH activity in the selected species provides an assay value which is a function of the amount of analyte in the test sample. Following a heterogeneous format, the bound- and free-species are separated and G6PDH activity measured in one thereof, whereas following a homogeneous format, G6PDH activity is measured directly in the reaction mixture without the need for separation.

DESCRIPTION OF THE PREFERRED EMBODIMENTS

Figure 1:
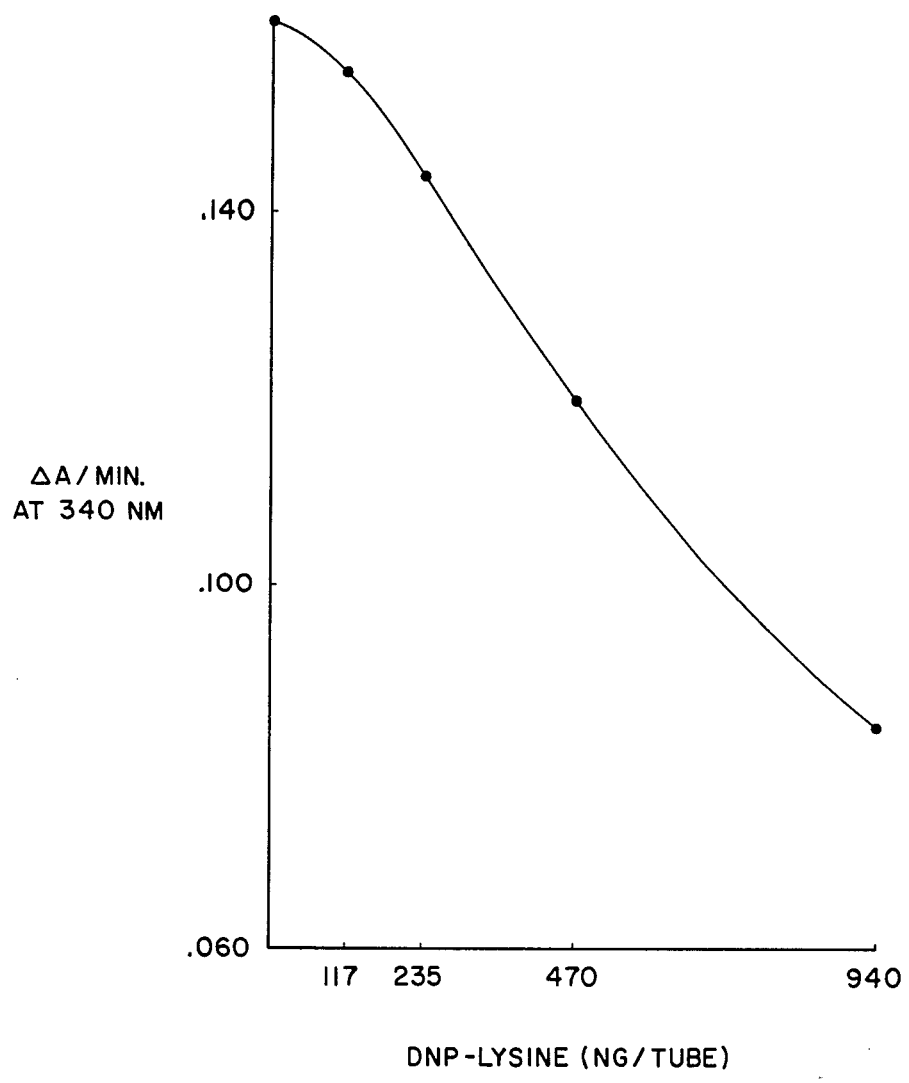
FIGS. 1-8 are standard curves for various assays performed according to the methods described in the examples below.

In the context of this disclosure, the following terms shall be defined as follows unless otherwise indicated:

Analyte—the substance, or class of related substances, whose presence or amount in a liquid medium is under determination.

Binding counterpart of the analyte—any substance, or class of substances, which has a specific binding affinity, normally reversible, for the analyte.

Specific binding analog of the analyte—any substance, or class of substances, which behaves similarly to the analyte with respect to binding by a binding counterpart of the analyte.

Reagent system—a composition, test device, test kit, or other physical arrangement or combination of reagents for use in performing the present assay method.

ANALYTE

The present assay can be applied to the detection of any analyte for which there is a specific binding counterpart available. The analyte usually is a peptide, polypeptide, protein, carbohydrate, glycoprotein, steriod, or other organic molecule for which a specific binding counterpart exists in biological systems or can be synthesized. The analyte, in functional terms, is usually selected from the group comprising antigens and antibodies thereto; haptens and antibodies thereto; and hormones, vitamins, metabolites and pharmacological agents, and their binding counterparts. Usually, the analyte is an immunologically-active polypeptide or protein, usually having a molecular weight of between about 1,000 and about 10,000,000, such as an antibody or antigenic polypeptide or protein, or a hapten having a molecular weight of at least about 100, and usually less than about 1,500.

Representative polypeptide analytes are angiotensin I and II, C-peptide, oxytocin, vasopressin, neurophysin, gastrin, secretin, bradykinin, and glucagon.

Representative protein analytes include the classes of protamines, mucoproteins, glycoproteins, globulins, albumins, scleroproteins, phosphoproteins, histones, lipoproteins, chromoproteins, and nucleo-proteins. Examples of specific proteins are prealbumin, $\alpha_1$-lipoproteins, human serum albumin, $\alpha_1$-acid glycoprotein, $\alpha_1$-antitrypsin, $\alpha_1$-glycoprotein, transcortin, thyroxine binding globulin, haptoglobin, hemoglobin, myoglobin, ceruloplasmin, $\alpha_2$-lipoprotein, $\alpha_2$-macroglobulin, $\beta$-lipoprotein, erythropoietin, transferrin, hemopexin, fibrinogen, the immunoglobulins such as IgG, IgM, IgA, IgD, and IgE, and their fragments, e.g., $F_c$ and $F_{ab}$, complement factors, prolactin, blood clotting factors such as fibrinogen, thrombin and so forth, insulin, melanotropin, somatotropin, thyrotropin, follicle stimulating hormone, leutinizing hormone, gonadotropin, thyroid stimulating hormone, placental lactogen, intrinsic factor, transcobalamin, serum enzymes such as alkaline phosphatase, lactic dehydrogenase, amylase, lipase, phosphatases, cholinesterase, glutamic oxaloacetic transaminase, glutamic pyruvic transaminase, and uropepsin, endorphins, enkephalins, protamine, tissue antigens, bacterial antigens, and viral antigens such as hepatitis associated antigens (e.g., $HB_sAg$, $HB_cAg$ and $HB_eAg$).

Representative hapten analytes include the general classes of drugs, metabolites, hormones, vitamins, and the like organic compounds. Haptenic hormones include thyroxine and triiodothyronine. Vitamins include vitamins A, B, e.g., $B_{12}$, C, D, E and K, folic acid and thiamine. Drugs include antibiotics such as aminoglycosides, e.g., gentamicin, tobramycin, amikacin, sisomicin, kanamycin, and netilmicin, penicillin, tetracycline, terramycin, chloromycetin, and actinomycetin; nucleosides and nucleotides such as adenosine diphosphate (ADP) adenosine triphosphate (ATP), flavin mononucleotide (FMN), nicotinamide adenine dinucleotide (NAD) and its phosphate derivative (NADP), thymidine, guanosine and adenosine; prostaglandins; steriods such as the estrogens, e.g., estriol and estradiol, sterogens, androgens, digoxin, digitoxin, and adrenocortical steriods; and others such as phenobarbital, phenytoin, primidone, ethosuximide, carbamazepine, valproate, theophylline, caffeine, propranolol, procainamide, quinidine, amitryptiline, cortisol, desipramine, disopyramide, doxepin, doxorubicin, nortryptiline, methotrexate, imipramine, lidocaine, procainamide, N-acetylprocainamide, amphetamines, catecholamines, and antihistamines.

ANTI-G6PDH

As used in the context of the present invention, the term "anti-G6PDH" shall be understood to mean an antibody capable of binding with G6PDH or a derivative or modification of such an antibody which retains the capability of binding with G6PDH. Thus, in general any substance which comprises one or more G6PDH-specific binding sites from an antibody can be used. Such antibody can be raised against whole or modified G6PDH by any available technique. Thus, an appropriate antibody source can be stimulated to produce anti-G6PDH by immunization with whole enzyme, aggregated or otherwise polymerized enzyme, enzyme fragments (e.g., by selecting antigenic determinants from the enzyme), synthetically prepared antigenic determinants, and so forth. In general, any source or form of G6PDH can be used, however, it is especially preferred to select a microbial source which produces an enzyme which can use a cofactor that is not effective with G6PDH endogeneous to the test sample, such as a mammalian body fluid. Microbial sources for G6PDH include *Leuconostoc mesenteriodes, Pseudomonas aeuroginosa, Hydrogenomonas* H 16, *Thiobacillus ferrooxidans,* and *Bacillus stearothermophilus.* Particularly preferred is G6PDH from *L. mesenteroides* (EC 1.1.1.49). which can use NAD as a cofactor whereas G6PDH from mammalian sources requires NADP.

When in the form of whole antibody, anti-G6PDH can belong to any of the classes and subclasses of known immunoglobulins, e.g., IgG, IgM, IgE, and so forth. Any fragment of any such antibody which retains specific binding affinity for G6PDH can also be employed, for instance, the fragments of IgG conventionally known as Fab, F(ab'), and F(ab')$_2$. In addition, aggregates, polymers, and conjugates of immunoglobulins or their fragments can be used where appropriate. Such poly(anti-G6PDH) can be prepared in any available manner so as to maintain binding affinity for G6PDH. Other forms of anti-G6PDH can be employed so long as the material selected has a specific binding affinity for G6PDH.

The immunoglobulin source for the anti-G6PDH can be obtained in any available manner. Usually, anti-G6PDH immunoglobulin will be obtained by conventional antiserum techniques or monoclonal techniques. Antiserum containing anti-G6PDH is obtained by well-established techniques involving immunization of an animal, such as a rabbit, guinea pig, or goat, with an appropriate immunogen. State-of-the-art reviews are provided by Parker, *Radioimmunoassay of Biologically Active Compounds,* Prentice-Hall (Englewood Cliffs, N.J., U.S.A., 1976), Butler, *J. Immunol. Meth.* 7: 1–24 (1975); Weinryb and Shroff, *Drug Metab. Rev.* 10: 271–283 (1975); Broughton and Strong, *Clin. Chem.* 22: 726–732 (1976); and Playfair et al, *Br. Med. Bull.* 30: 24–31 (1974). Such antibodies can also be obtained by somatic cell hybridization techniques, such antibodies being commonly referred to as monoclonal antibodies. Reviews of monoclonal antibody techniques are found in *Lymphocyte Hybridomas,* ed. Melchers et al, Springer-Verlag (New York 1978), *Nature* 266: 495 (1977), *Science* 208: 692 (1980), and *Methods in Enzymology* 73 (Part B): 3–46 (1981).

LABELED CONJUGATE

The labeled conjugate comprises two principal components which are associated or linked to one another, e.g., by direct chemical linkage such as involving covalent bonds, or by indirect linkage such as by incorporation of one component, usually the label, in a microcapsule or liposome which in turn is chemically linked to the other component. One component of the labeled conjugate is the binding component, whose function is well-known in the art. The binding component participates in the specific binding reaction system with any analyte present in the reaction mixture. Depending on the particular assay format followed, the binding component will usually be the analyte itself, a specific binding analog of the analyte, or a binding counterpart of the analyte. Selection of the binding component for a particular assay and the methods for incorporating same into the labeled conjugate are matters of ordinary skill in the art.

The other component of the labeled conjugate is the novel label component of the present invention, anti-G6PDH. When chemical bonds are involved in linkage, the important considerations on a general level for choosing the sites of attachment on the binding component and the label are (1) preservation of the ability of the linked binding component to participate effectively in the selected binding assay system, and (2) preservation of the ability of the linked anti-G6PDH label to modulate the catalytic activity of G6PDH, in both cases, to the extent that a useful assay will result for the particular analyte under assay and for the particular concentrations in which such is to be detected. Usually, a linking group will comprise a chemical bond, usually a single bond, or a chain containing between 1 to 20, more commonly 1 to 10, carbon atoms and 0 to 10, more commonly 1 to 5, heteroatoms selected from nitrogen, oxygen, and sulfur. Further details regarding the selection of linking groups may be found in the references cited hereinabove, e.g., U.S. Pat. Nos. 4,238,565 and 3,817,837.

In the most usual case, the anti-G6PDH label of the present invention and the binding component to be coupled therewith will have available amino and carboxyl functionalities for coupling by conventional peptide condensation reactions. As a protein, anti-G6PDH will have numerous active amino and carboxyl groups to participate in peptide condensation. Oftentimes, the analyte will itself contain an amino or carboxyl group useful for coupling to the label by peptide condensation, such as where the analyte is a protein or polypeptide or is a hapten that is a primary amine or carboxylic acid. Where the analyte does not have an available functionality for coupling to the label, such can be readily introduced by forming an amino or carboxyl derivative of the analyte. Typical analyte derivatives of this type (i.e., specific binding analogs of the analyte) and further details concerning the formation of a labeled conjugate by peptide condensation and equivalent techniques are provided in U.S. Pat. No. 4,226,992, particularly in columns 3-10 thereof.

Conventional peptide condensation reactions include the carbodiimide reaction [*Science* 144: 1344 (1964)], the mixed anhydride reaction [Erlanger et al, *Methods in Immunology and Immunochemistry*, ed. Williams and Chase, Academic Press (New York 1967) p. 149], and the acid azide and active ester reactions [Kopple, *Peptides and Amino Acids*, W. A. Benjamin, Inc. (New York 1966)]. See also for a general review *Clin. Chem.* 22: 726 (1976)].

It will be recognized, of course, that other well known methods are available for coupling the analyte and label to form the labeled conjugate of the present invention. For example, bifunctional reactions can be used to couple amines to amines, e.g., bis-isocyanates, bis-imidoeters, and glutaraldehyde [*Immunochem.* 6: 53 (1969)]. Of course, functional groups on the analyte, or binding analog thereof, and on the label other than amino and carboxyl groups can be used as the site of attachment depending on the synthetic approach selected. These synthetic routes are available to one of ordinary skill in the art from the literature.

ASSAY TECHNIQUES

In broad principle, the present assay method can be performed according to any of the conventional homogeneous or heterogeneous formats. However, in those circumstances where the modulation effect produced by the labeled conjugate is essentially indistinguishable between the bound-species and the free-species, a heterogeneous format will have to be followed in order to perform an assay.

1. Homogeneous Formats

In the homogeneous assay technique, i.e., an assay technique which does not require a physical separation of the bound-species and the free-species, reaction between the binding component in the labeled conjugate and a corresponding binding counterpart causes a measurable change, either in a positive or a negative sense, in the modulation effect of anti-G6PDH on G6PDH in the reaction mixture. The distribution of the labeled conjugate between the bound-species and the free-species is differentiated by the inability or altered ability of the modulator to affect enzyme activity when in the bound-species. Several manipulative techniques are available for carrying out a homogeneous assay with the most common technique being the competitive binding technique. In the competitive binding technique, the liquid medium is combined with a binding counterpart of the analyte, a labeled conjugate comprising anti-G6PDH coupled to the analyte or a specific binding analog thereof, and G6PDH, and thereafter measuring G6PDH activity in the reaction mixture. The homogeneous competitive binding technique is generally applicable to the determination of most analytes, including antigenic proteins and polypeptides and haptens. Antibodies can be determined as antigenic proteins by using an anti-antibody antibody to recognize and bind with any antibody under assay. This antibody assay will be class specific and will not distinguish antibodies according to their antigen specificities.

In order to determine antibodies, or other binding proteins, receptors, or binding materials in general, according to their antigen or counterpart specificities, a direct technique can be used. The liquid medium is combined with a labeled conjugate comprising anti-G6PDH coupled to a binding counterpart of the analyte, and G6PDH, and thereafter G6PDH activity is again measured in the reaction mixture. In this case, the analyte can be antibodies having specificity for a particular antigen or hapten (which serves, in its native form or a binding analog form, as the binding counterpart in the labeled conjugate), or can be the binding capacity of the test sample to bind a particular substance due to the presence in the sample of a particular binding protein, receptor, carrier substance, or the like, e.g., triiodothyronine or thyroxine binding capacity ($T_3$ uptake or $T_4$ uptake).

In general, when following the homogeneous assay technique, the components of the assay reaction, i.e., the liquid medium suspected of containing the analyte, the labeled conjugate, G6PDH, and, if necessary, a binding counterpart of the analyte, can be combined in any amount, manner, and sequence, provided that G6PDH activity is measurably altered when the liquid medium contains the analyte in an amount of concentration of significance to the purposes of the assay. Preferably, all of the components of the specific binding reaction are soluble in the liquid medium. Additionally, the reaction mixture will be formed to contain a conventional indicator composition which produces a detectable response, e.g., light absorption, color, fluorescence, chemiluminescence, and so forth, as a function of the catalytic activity of G6PDH.

2. Heterogeneous Formats

The present assay method can also be applied to the conventional heterogeneous type assay techniques wherein the bound- and free-species of the labeled conjugate are separated and the label component in one or the other is determined. The reagent means for performing such a heterogeneous assay can take many different forms. In general, such means comprises three basic constituents, which are (1) the analyte to be detected, (2) a binding counterpart of the analyte and (3) the labeled conjugate. The binding reaction constituents are combined simultaneously or in a series of additions, and with an appropriate incubation period or periods, the labeled conjugate becomes bound to its corresponding binding partners such that the extent of binding, i.e., the ratio of the amount of labeled conjugate bound to a binding counterpart (the bound-species) to that unbound (the free-species), is a function of the amount of analyte present. The bound- and free-species are physically separated and the amount of label present in one thereof is determined by measuring the G6PDH activity therein and comparing such to a negative control or standard results, e.g., a standard curve.

Various means of performing the separation step and of forming the binding reaction systems are available in the art. Separation can involve such conventional techniques as those using a solid-phase antibody or antigen, a second antibody, or a solid-phase second antibody, as well as the use of immune complex precipitation agents, adsorbents, and so forth. Binding reaction systems that can be followed include the so-called competitive binding technique, the sequential saturation technique, the "sandwich" technique, and so forth. Further details concerning the various known heterogeneous systems are readily available in the literature, e.g., U.S. Pat. No. 4,230,797.

It is contemplated that manipulative schemes involving other orders of addition and other binding reaction formats can be devised for carrying out homogeneous and heterogeneous specific binding assays without departing from the inventive concept embodied herein.

REACTION MIXTURE

The liquid medium to be assayed can be a naturally occurring or artificially formed liquid suspected to contain the analyte, and usually is a biological fluid or a dilution thereof. Biological fluids that can be assayed include serum, plasma, urine, saliva, and amniotic and cerebrospinal fluids.

The binding reaction will, in almost all cases, be allowed to proceed under mild conditions. The reaction mixture will be in general an aqueous medium with any desirable organic cosolvents being present in minor amounts. The temperature of the reaction will be maintained at a constant level in normal circumstances throughout the incubation period and the enzyme measurement step. Temperatures will generally be between 5° and 50° C., more usually between 20° and 40° C. Preferably, the reaction will proceed at room temperature. The pH of the reaction mixture will vary between 5 and 10, more usually between 6 and 9. The concentration of various reagents will depend on the level of analyte expected in the test medium, with such level usually being between $10^{-3}$ and $10^{-12}$M. As in the case of the previously described reaction parameters, selection is primarily based on empirically derived optimization balanced against the preferences and needs of the technician who will ultimately perform assays on a routine basis. None of the parameters therefore is of a critical nature to the present invention, rather they are all within the ordinary skill in the art.

REAGENT SYSTEM

The reagent system of the present invention comprises all of the essential chemical elements required to conduct a desired assay method encompassed by the present invention. The reagent system is presented in a commercially packaged form, as a composition or admixture where the compatibility of the reagents will allow, in a test device configuration, or as a test kit, i.e., a packaged combination of one or more containers holding the necessary reagents. Included in the reagent system are the reagents appropriate for the binding reaction system desired, always requiring an anti-G6PDH labeled conjugate and G6PDH. Such binding reaction reagents can include, in addition to the labeled conjugate, a binding counterpart to the analyte, the G6PDH indicator composition, and so forth. Of course, the reagent system can include other reagents as are known in the art and which may be desirable from a commercial and user standpoint, such as buffers, diluents, standards, and so forth.

The present invention will now be illustrated, but is not intended to be limited, by the following examples:

EXAMPLES

I. Reagents

A. List of Materials

Glucose-6-phosphate dehydrogenase (G6PDH) from *Leuconostoc mesenteroides* (EC 1.1.1.49), 759 International Units per milligram (I.U./mg), was purchased from the Oriental Yeast Co., Osaka, Japan.

Antibody to G6PDH (Anti-G6PDH) was raised in rabbits against G6PDH as immunogen according to the method of Roda and Bolelli, *J. Steroid Biochem.* 13: 449–454 (1980) which is based on the method of Vaitukaitis et al, *J. Clin. Endocrinol.* 33:988 (1981).

Diaphorase (NADH dye oxidoreductase, E.C. 1.6.99), 37 U/mg, was obtained from Toyo Jozo Co., Ltd., Tokyo, Japan.

Nicotinamide adenine dinucleotide (NAD), nicotinamide adenine dinucleotide phosphate (NADP), and glucose-6-phosphate (G6P) were obtained from Boehringer Mannheim, GmbH, West Germany.

Nitro blu tetrazolium, oxamic acid sodium salt, avidin from egg white, and biotin were obtained from Sigma Chemical Co., St. Louis, Mo., U.S.A.

N-Hydroxysuccinimidobiotin (NHS-Biotin) was obtained from Pierce Eurochemie BV, Rotterdam, Holland.

Antibody to dinitrophenyl (anti-DNP) produced in rabbits; human IgG; and anti-human IgG ($\gamma$-chain specific) produced in goats were obtained from Miles-Yeda, Ltd., Rehovot, Israel.

Dinitrofluorobenzene (DNFB) and a conjugate of dinitrophenyl (DNP) and lysine (DNP-lysine) were obtained from Serva Fenbiochemica, Heidelberg, West Germany.

B. Purification of Anti-G6PDH

Whole antiserum was treated with 50% ammonium sulfate [$(NH_4)_2SO_4$] followed by gel filtration chromatography on Ultragel AcA 44 (LKB, Bromma, Sweden).

C. Preparation of DNP-Anti-G6PDH Conjugate

To a stirred solution of 2.56 milligrams (mg) of anti-G6PDH in 1.5 milliliters (ml) of phosphate buffer 0.1M, pH 7.4, at room temperature 400 microliters ($\mu$l) of DNFB (5 mg/ml) in absolute ethanol were added. The addition of DNFB was performed stepwise in aliquots of 50 $\mu$l every 20 minutes. After the addition of 100, 200, 300, 400 $\mu$l of DNFB, 10 $\mu$l of the reaction mixture were withdrawn, diluted in 0.1M Tris [tris(hydroxymethyl)-aminomethane] buffer, pH 7.9, containing 0.5% of bovine serum albumin (BSA) and assayed for the immunoreactivity towards the enzyme in absence of anti-DNP and towards the anti-DNP using an excess of anti-DNP.

When further addition of DNFB did not increase the immunoreactivity towards the anti-DNP, the reaction mixture was filtered on Sephadex G25 (Pharmacia, Uppsala, Sweden), diluted 1:2 with Tris buffer containing 0.5% of BSA and stored at 5° C.

D. Preparation of Biotin-Anti-G6PDH Conjugate

The conjugation of biotin to the IgG anti-G6PDH was carried out substantially in the same way as for the conjugation of DNFB.

To a stirred solution (2.5 ml) of 0.1M phosphate buffer, pH 7.6, containing 5.35 mg of anti-G6PDH, aliquots of 10 $\mu$l of NHS-Biotin (8 mg/ml) in anhydrous dimethyl formamide (DMF) were added at intervals of 20 minutes. For monitoring the conjugate formation twenty minutes after every addition of NHS-Biotin, 10 μl of the reaction mixture were withdrawn, diluted in Tris buffer containing BSA 0.5% and assayed for the immunoreactivity in the presence and in the absence of an excess of avidin. The conjugation reaction was continued until the conjugate had lost, at maximum, 10-20% of its native immunoreactivity and reached about 50% of reactivation in the presence of an excess of avidin. The conjugate was then filtered on Sephadex G25, equilibrated and eluted with Tris HCl buffer. The eluate was dialyzed for 24 hours against the same buffer and stored at 4° C. in presence of 0.5% BSA.

E. Preparation of Human IgG-Anti-G6PDH Conjugate

This conjugate was prepared according to the method of Murayama et al, *Immunochem.* 15:523 (1978).

A 1 ml volume of phosphate buffer, 0.05M, pH 7.4, containing 5.35 mg of anti-G6PDH was adjusted to pH 4 with dilute acetic acid. To this solution was added 0.1 ml of 0.2M sodium periodate ($NaIO_4$) in acetate buffer, 0.01M, pH 4. After 25 minutes, 50 μl of ethylene glycol were added and the solution filtered on a Sephadex G25 column. To this activated anti-G6PDH, 2 ml of human IgG (70 mg of powder) in carbonate buffer, 0.1M, pH 9.5, were added and the pH of the resulting solution immediately brought to and maintained at pH 9.5. After 2.5 hours, 1.5 mg of sodium borohydride ($NaBH_4$) was added and the reaction incubated for a further 40 minutes at 4° C. The solution was then ultrafiltered and chromatographed on Sephacril S300 (Pharmacia). The fractions immunologically reactive towards both the enzyme and the antihuman IgG were pooled.

II. Assay Methods

A. Assay for Haptens with U.V. read-out

DNP-Lysine assay

To each of a series of plastic test tubes were added in sequence:

0.1 ml DNP-Lysine standard (0-9.4 μg/ml in 0.1M Tris-HCl, pH 7.9, containing 0.5% of BSA and 0.05% sodium azide;

0.1 ml DNP-anti-G6PDH conjugate in Tris buffer, at a concentration giving 80% inhibition of the enzyme in absence of anti-DNP; and 0.2 ml anti-DNP/G6PDH mixture, in Tris buffer, containing anti-DNP diluted 1:2 and G6PDH at a concentration giving $\Delta A/_{min}=0.580$ in absence of the conjugate.

The tubes were incubated for 15 minutes at room temperature, and 0.6 ml of substrate/indicator solution was added to each tube. The substrate/indicator solution consisted of 5.3 mM NAD and 18.2 mM G6P in Tris-HCl buffer, pH 7.9. The reaction mixture was immediately aspirated into a thermostated (30° C.) photometer flow cell and the initial enzyme catalyzed reaction rate was measured at 340 nanometers (nm) using delay and reading times of 30 seconds each.

Biotin assay

To each of a series of plastic test tubes were added in sequence:

0.1 ml Biotin standard (0-320 ng/ml) in 0.1M Tris-HCl, pH 7.9, containing 0.5% BSA and 0.5% sodium azide;

0.1 ml Biotin-anti-G6PDH conjugate, in Tris buffer at a concentration giving 80% inhibition of the enzyme in absence of avidin; and 0.2 ml Avidin/G6PDH mixture, in Tris buffer, containing 18 μg/ml of avidin and G6PDH at a concentration giving $\Delta A/_{min}=0.580$ in absence of the conjugate.

The tubes were incubated for 60 minutes at room temperature before adding the substrate indicator solution and reading as for DNP-Lysine assay.

B. Assay for Hapten with Colorimetric Read-out

To each of a series of plastic test tubes were added in sequence:

0.1 ml Biotin standard (0-80 ng/ml) in 0.1M Tris-HCl buffer, pH 7.9, containing 0.5% BSA and 0.05% sodium azide;

0.1 ml Biotin-anti-G6PDH conjugate in Tris buffer, at a concentration giving 80% inhibition of the enzyme in absence of avidin; and 0.2 ml Avidin/G6PDH/diaphorase mixture containing 4.4 μg/ml of avidin, G6PDH at a concentration giving $\Delta A/_{20\ min}=2.3$ and 100 μg/ml of diaphorase.

After a 40 minute incubation at room temperature, 0.2 ml of a substrate/indicator solution containing 18.7 mM NAD, 1.9 mM NBT and 65 mM G6P in 33 mM phosphate citrate buffer, pH 5.7, were added to each tube and the tubes incubated for an additional 20 minutes at room temperature. The reaction was then stopped by addition of 0.5 ml of 1M hydrochloric acid (HCl) containing 1% Triton X-100 detergent and the absorbance measured at 580 nm.

C. Assay for Antigen with Colorimetric Read-out

To each of a series of plastic test tubes were added in sequence:

0.1 ml 1:41 diluted human IgG standard, calibrated against a reference serum (Technicon Chemicals, Tournai, Belgium) in 0.1M Tris-HCl buffer, pH 7.9, containing 0.5% BSA and 0.05% sodium azide. Before 1:41 dilution, the concentrations of the standards ranged from 0 to 27.4 mg/ml; and 0.2 ml anti-human IgG/G6PDH/diaphorase mixture containing anti-human IgG dilute 1:2.25, G6PDH giving $\Delta_{A/20\ minutes}=1.44$ in absence of the anti G6PDH conjugate and diaphorase 100 μg/ml in Tris buffer.

The tubes were incubated for 15 minutes at room temperature, then 0.2 ml of human IgG-anti-G6PDH conjugate, at the concentration giving enzyme inhibition of 80%, was added to each, followed by a further incubation for 40 minutes at room temperature. Then 0.2 ml of the substrate/indicator solution was added. The reaction was stopped after 20 minutes by addition of 0.5 ml of 1M HCl containing 1% Triton X-100 and the absorbance read at 580 nm.

III. RESULTS

A. Standard Curve for U.V. Rate Assay for DNP-Lysine

A standard curve (FIG. 1) relating DNP-lysine concentrations to rate of absorbance change at 340 nm (ΔA/min at 340 nm) was constructed following the assay method described in Part II-A above.

B. Standard Curve for U.V. Rate of Assay for Biotin

Figure 2:
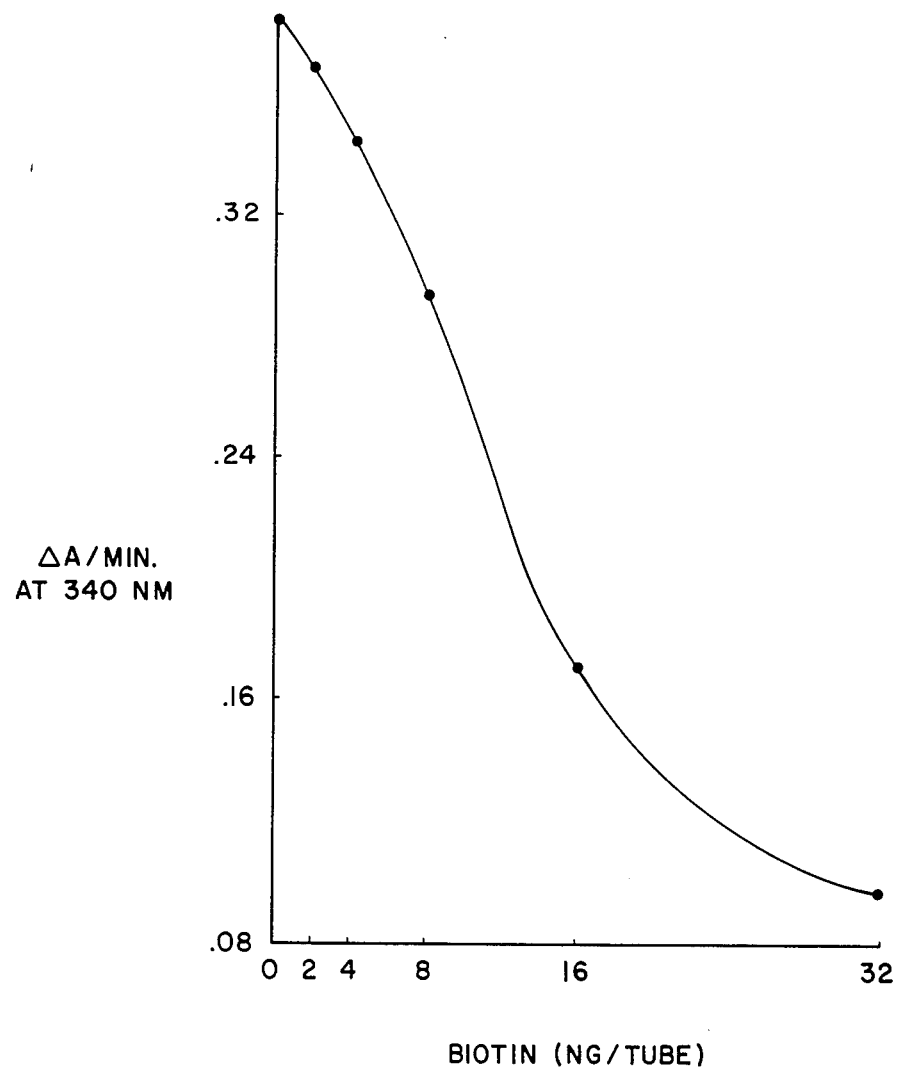

A standard curve (FIG. 2) relating biotin concentrations to ΔA/min at 340 nm was contructed following the assay method described in Part II-A.

C. Standard Curve for Colorimetric End-Point Assay for Biotin

Figure 3:
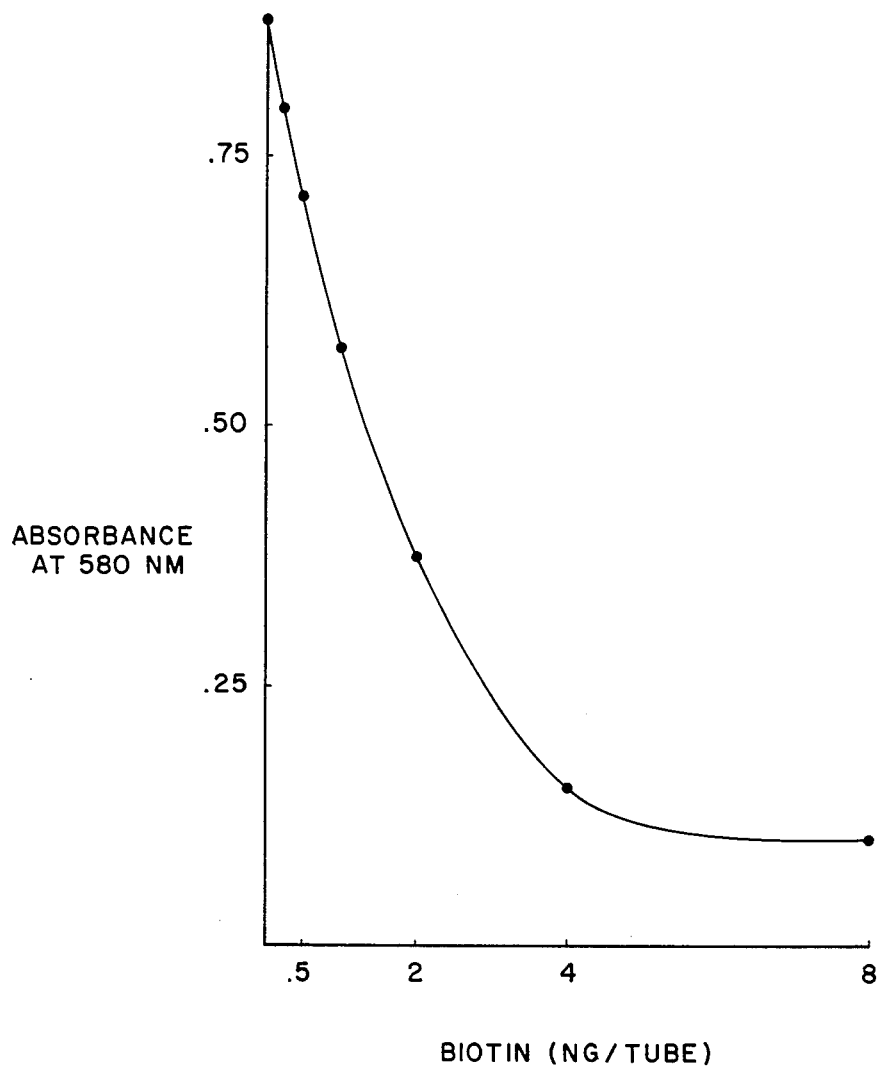

A standard curve (FIG. 3) relating biotin concentration to end-point absorbance at 580 nm was constructed following the method described in Part II-B above. The blank value for absorbance of the reaction mixture in the absence of G6PDH was 0.040 and was subtracted from assay values.

D. Standard Curve for Colorimetric End-Point Assay for Human IgG

Figure 4:
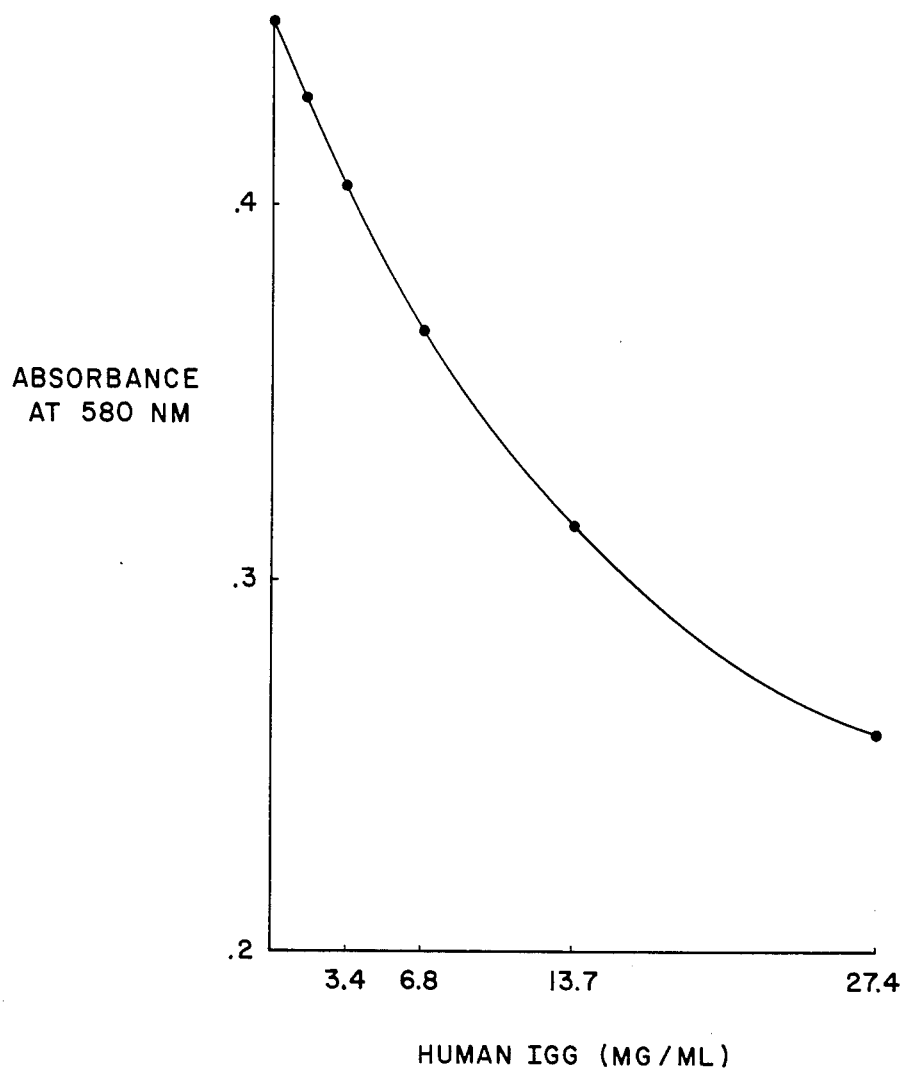

A standard curve (FIG. 4) relating to human IgG concentration to end-point absorbance at 580 nm was constructed following the method described in Part II-C above.

A correlation study with an immunoturbidimetric method (ITA) was conducted on 20 serum samples. The correlation was: present method=0.95+1.13 ITA; r=0.864.

IV. Interferences Study

A. Interferences with the Enzymatic Reaction
1. Serum Interferences

When 50 μl of human serum were incorporated in the assay, the enzyme activity was 25% higher than that in the buffer alone. This positive interference was found to be due primarily to endogeneous lactate and lactic dehydrogenase (LDH) which reduces NAD and, in turn, NBT. The addition of oxamic acid, an inhibitor of lactic dehydrogenase, completely inhibited the LDH without affecting the performance of the assay. However, the test in the presence of 50–100 μl of serum still gave an activity higher than that in buffer, due to other unidentified interferants.

To investigate the maximum variability of these interferences, the G6PDH activity ($\Delta A_{20\ min}=0.282$ in buffer) was measured in presence of 100 μl of 18 turbid, emolized, or icteric human sera. Oxamic acid was included in the assay. The results are shown in Table 1.

TABLE 1

| | Absorbance at 580 nm/20 min. | |
|---|---|---|
| Medium | Blank | Sample |
| Buffer | 0.020 | 0.282 |
| Sera | | |
| $\bar{x}$ | 0.055 | 0.349 |
| SD | 0.016 | 0.017 |
| CV | 29 | 4.87 |
| n | 18 | 18 |

In Table 1 above, the symbols are defined as follows:
$\bar{X}$—average value
SD—standard deviation
CV—coefficient of variation
n—number of data points collected.

For the purpose of eliminating the positive serum interferences on the colorimetric read-out method still existing in presence of oxamate, the effects of Triton X-100 on the spectrum of the color developed after the enzymatic colorimetric reaction were investigated. The experiments were carried out incorporating in the G6PDH assay varying concentrations of Triton X-100 in the presence and in the absence of 100 μl of human serum, and recording the spectra of the color formed after stopping. A 0.7 ml volume of a solution of 11.4 ng/ml of G6PDH in 0.1M Tris-HCl, pH 7.9, containing 1% BSA, 38 mM oxamic acid and 14.3 μg/ml diaphorase were mixed with 200 μl of a solution of substrate/indicator solution consisting of 18.7 mM NAD, 65 mM G6P, 1.9 mM NBT and varying concentrations of Triton X-100 in 33 mM phosphate-citrate buffer, pH 5.7. The reactions were allowed to proceed for 20 minutes at room temperature, then stopped with 1M HCl containing 1% Triton X-100 and the spectrum of each solution recorded between 660 and 480 nm. One series of assay test tubes contained the reagents and 100 μl of a pool of human serum, the other one reagent and 100 μl of buffer in place of serum.

Table 2 shows the results, where the concentration of Triton X-100 is that in the reaction mixture before stopping, and λmax is the wavelength of the maximum absorption.

TABLE 1

| | MEDIUM | | | |
|---|---|---|---|---|
| | Buffer | | Serum | |
| Conc. of Triton X-100 g/100 ml | ΔA/20 min. at 580 nm | λmax nm | ΔA/20 min. at 580 nm | λmax nm |
| 0.25 | 1.047 | 528 | 1.284 | 536 |
| 0.5 | 1.093 | 524 | 1.198 | 526 |
| 1.0 | 1.214 | 526 | 1.254 | 526 |
| 2.0 | 1.414 | 528 | 1.428 | 528 |
| 4.0 | 1.511 | 528 | 1.527 | 528 |

The recorded spectra revealed a substantial identity between serum and buffer at the concentration of 2 and 4% of Triton. The color development, recorded in a subsequent experiment at 580 nm using 2% Triton, showed the same $\Delta A/_{min}$ both for assay in serum and in buffer.

A final experiment, to assess the serum interferences and their variability, was carried out measuring the activity of a fixed concentration of G6PDH, by the colorimetric read-out, in the absence and in the presence of 50 μl of 36 human sera at the optimized concentrations of Triton and oxamate.

To each test tube was added:
50 μl buffer or serum
500 μl 0.1M Tris-HCl buffer, pH 7.9, containing 0.5% BSA, 0.05% sodium azide, A/20 min.=1.333 G6PDH, 20 μg diaphorase, 34 mM oxamic acid; and
200 μl substrate/indicator solution consisting of 33 mM phsosphate-citrate buffer, pH 5.7, 7 g/100 ml Triton X-100, 18.7 mM NAD, 65 mM G6P and 1.9 mM NBT.

The mixture was incubated for 20 minutes at room temperature then stopped with 0.5 ml of 1M HCl containing 1% Triton X-100. The results reported in Table 3 confirm that the serum interferences were negligible.

TABLE 3

| | MEDIUM | | | |
|---|---|---|---|---|
| | Buffer | | Serum | |
| | Blank | Sample | Blank | Sample |
| $\bar{X}$ abs. | 0.0295 | 1.3338 | 0.0366 | 1.328 |
| SD abs. | 0.0005 | 0.0100 | 0.0023 | 0.0134 |
| CV | 1.7 | 0.82 | 6.3 | 1.0 |
| n | 10 | 36 | 36 | 36 |

2. Drugs, Metabolites, and Urine Interferences

Some possible interfering substances were also tested in the enzymatic assay. The assays were performed with the standard method using 50 μl of the solution at the concentration of substance indicated in Table 4 in a final volume, before stopping, of 0.65 ml. Only ascorbic acid gave strong interferences which, however, can be eliminated by various known means, including the addition of a low concentration of the enzyme ascorbate oxidase.

TABLE 4

| Potential Interferent | No interference up to: (mg %) |
|---|---|
| Uric Acid | 40 |
| Urea | 400 |
| Bilirubin | 20 |
| Ascorbic Acid | 2 |
| Glucose | 1000 |
| Sodium Fluoride | 400 |
| Sodium Oxalate | 400 |
| Sodium Citrate | 760 |
| Sodium Heparinate | 150 |
| EDTA | 200 |
| Acetylsalicylic Acid | 12 |
| Gentisic Acid | 10 |
| L-Dopa | 0.5 |
| Urine (normal) | 25 μl |

B. Interferences with the Immunological Reaction

To assess the serum effect on the immunological reaction, 50 μl of 36 human sera were incorporated in the assay for the G6PDH-antiG6PDH reaction.

To each test tube was added:

50 μl buffer or serum

250 μl Fab anti-G6PDH-cortisol (see Part VIII below) conjugate (see Part VII below) at a concentration giving 70% enzyme inhibition, in 0.1M Tris buffer, pH 7.9, containing 0.5% BSA, 0.05% sodium azide and 34 mM oxamic acid;

250 μl G6PDH/diaphorase mixture in Tris buffer containing G6PDH giving $\Delta A/20\ min = 2.670$ and 20 μg of diaphorase After incubation of 60 minutes was added:

200 μl substrate/indicator solution at concentrations and conditions as indicated in part 1-A (final experiment).

The summarized data reported in Table 5 show the low effect and variability of serum interferences on the immunological reaction between G6PDH and anti-G6PDH-cortisol conjugate.

TABLE 5

|  | MEDIUM | |
|---|---|---|
|  | Buffer | Serum |
| $\bar{X}\ \Delta A/20\ min$ | 0.8036 | 0.8276 |
| SD ΔA/20.min | 0.0062 | 0.0131 |
| CV | 0.77 | 1.58 |
| n | 36 | 36 |

V. Stability Study

A. Enzyme Mixture (G6PDH/diaphorase)

| Storage temperature | 4° C. | 25° C. | 40° C. | | |
|---|---|---|---|---|---|
| Days | 35 | 35 | 5 | 9 | 21 |
| % Residual Acitivity | 95.2 | 85 | 71.6 | 54.5 | 30 |

B. Labeled Conjugate

No detectable loss of immunoreactivity after five months of storage 15 times more concentrated, at 4° C.

C. Substrate/Indicator Mixture

The mixture of substrates and chromogen (NAD, G6P and NBT) was kept, every day, for 16 hours at 4° C., and 8 hours at 22° C. on the laboratory bench for one month. The absorbance of this solution increased only from 0.012 to 0.025 at 580 mn, without affecting the performance of the enzymatic assay. The same solution stored at 4° C. for five months is also stable (the absorbance increases from 0.012 to 0.022).

VI. Purification of Anti-G6PDH by Affinity Chromatography

The immunoadsorbent, Sepharose 4B (2 g) linked to G6PDH (27 mg), was prepared according to the manufacturer's instructions (Pharmacia, Sweden) and packed into a small column. A 10 ml volume of rabbit antiserum was precipitated with $(NH_4)_2SO_4$ at the final saturation of 40%. The IgG precipitated (100.9 mg) was centrifuged, dissolved in 0.1M phosphate buffer, pH 8, dialyzed against the same buffer and passed through the immunosorbent. The column was washed with the starting buffer (0.1M phosphate, pH 8), $H_2O$, acetic acid, pH 4, containing 0.5M NaCl and the specific IgG anti-G6PDH eluted in two steps; with acetic acid, pH 2.3, containing NaCl 0.5M and acetic acid, pH 2.3. The amount of affinity purified IgG was 9 mg with a purification factor of 4.

VII. Highly Sensitive Cortisol Assay

A. Reagents

Antibody to cortisol (Anti-cortisol) was raised in rabbits against cortisol-3-carboxymethyl-oxime-BSA (Analytical Antibodies, Milan, Italy).

Purified anti-G6PDH from Part VI above.

Cortisol-anti-G6PDH conjugate was prepared as follows:

Mixed anhydride: 5 mg of cortisol-3-CMO (11 μmol) were dissolved at room temperature in 1.5 ml of dioxane containing 2.5 μl of N-methylmorpholine (35 μmol). The solution was cooled to 12° C. and 10 μl of isobutyl chloroformate (13 μmol) added under stirring. Portions (5 μl) of the resulting mixed anhydride were added to a 1.5 ml solution of affinity purified IgG anti-G6PDH (0.5 mg/ml) in carbonate-bicarbonate buffer, 0.1M, pH 9.2. A total of 85 μl of mixed anhydride was added and the antibody lost about 35% of its initial immunoreactivity toward the enzyme. The reaction mixture was chromatographed on Sephadex G-25 and the substitution degree was 13.2 as calculated according to the Erlanger method, *J. Biol. Chem.* 228: 713 (1957).

All other reagents were as described in Part I above.

B. Assay Method

Figure 5:
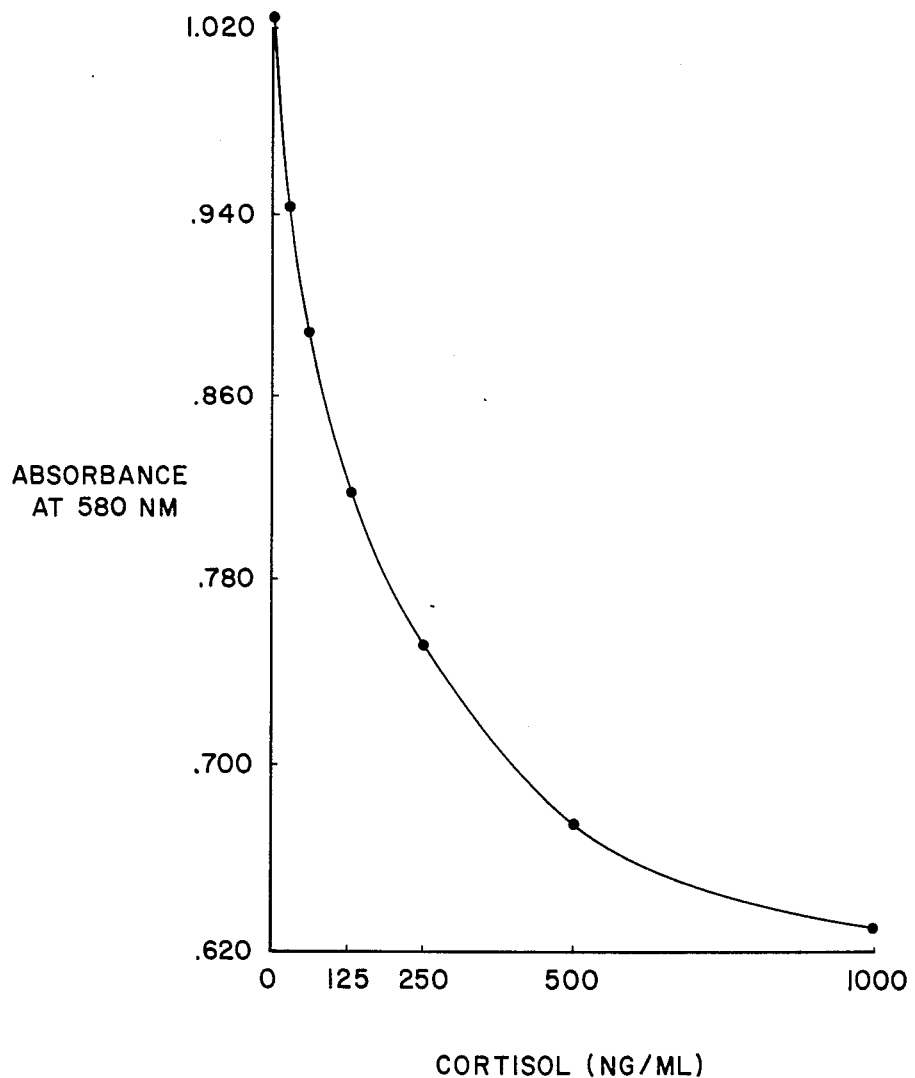

Reaction mixtures were prepared by combining 300 μl of Tris buffer, pH 7.9, containing 1.3 mg salicylate (as blocking agent for serum protein binding), 3 mg oxamate, and cortisol-anti-G6PDH diluted 1:48; 300 μl of Tris buffer, pH 7.9, containing 13.3 mg G6PDH, 20 μg diaphorase, and anti-cortisol diluted 1:900; and 50 μl of cortisol standards in the concentrations shown on the abscissa of FIG. 5 of the drawings. After incubation for 60 minutes at room temperature, 200 μl of a substrate/indicator solution were added. The substrate/indicator solution was as described in Part II-B. The reaction mixtures were incubated an additional 20 minutes and the reactions stopped by addition of 0.5 ml of 1M HCl. The absorbance at 580 nm was read. The standard curve is shown in FIG. 5 of the drawing.

C. Results

The assay was observed to be sensitive to cortisol in the range of 10 ng/ml. Correlations were made with a standard RIA method with the following results: y=36.5+1.26X, r=0.985, n=17.

VII. Use of Fab Fragment As Anti-G6PDH Label

A. Isolation and Purification of Fab

The cleavage of the IgG anti-G6PDH was performed substantially according to the method described by Porter [*Biochem. J.* 73: 119(1959] as follows:

A 334 mg portion of IgG obtained by 40% saturation of $(NH_4)_2SO_4$ and dialyzed against 0.1M phosphate buffer pH 6, were incubated overnight at 37° C. with 340 mg of Papain (Sigma, E.C. 3.4.22.2) in a final solution of dialysis buffer of 13 ml containing 10 mM cysteine and 2 mM EDTA. The resultant digest was dialyzed against water and then against 0.1M phosphate buffer, pH 8. The dialyzed solution was centrifuged and affinity chromotagraphed on Sepharose-G6PDH immunoadsorbent as described in Part VI above. A 7.4 mg portion of pure Fab was obtained and, as can be seen in Table 6, Fab retained the property to inhibit the enzyme.

TABLE 6

Anti-G6PDH titer at different steps of purification

| Steps | Titer ng/ml |
|---|---|
| IgG $(NH_4)_2SO_4$ | 1250 |
| Digested | 1880 |
| Fab affinity purified | 100 |

The titer was defined as the final concentration in ng/ml of anti-G6PDH required to inhibit the enzyme (22.4 ng/ml) by 90%, using the colorimetric method.

B. Conjugation of Cortisol 3-CMO to the Fab fragment of IgG anti-G6PDH

The Fab-cortisol conjugate was successfully prepared using the mixed anhydride method, as described for IgG-cortisol conjugate (see Part VII-A above). The conjugate Fab retained 57% of the immunoreactivity of the unmodified Fab. The cortisol/Fab mol ratio was 10.5.

C. Standard curve for cortisol assay

Figure 6:
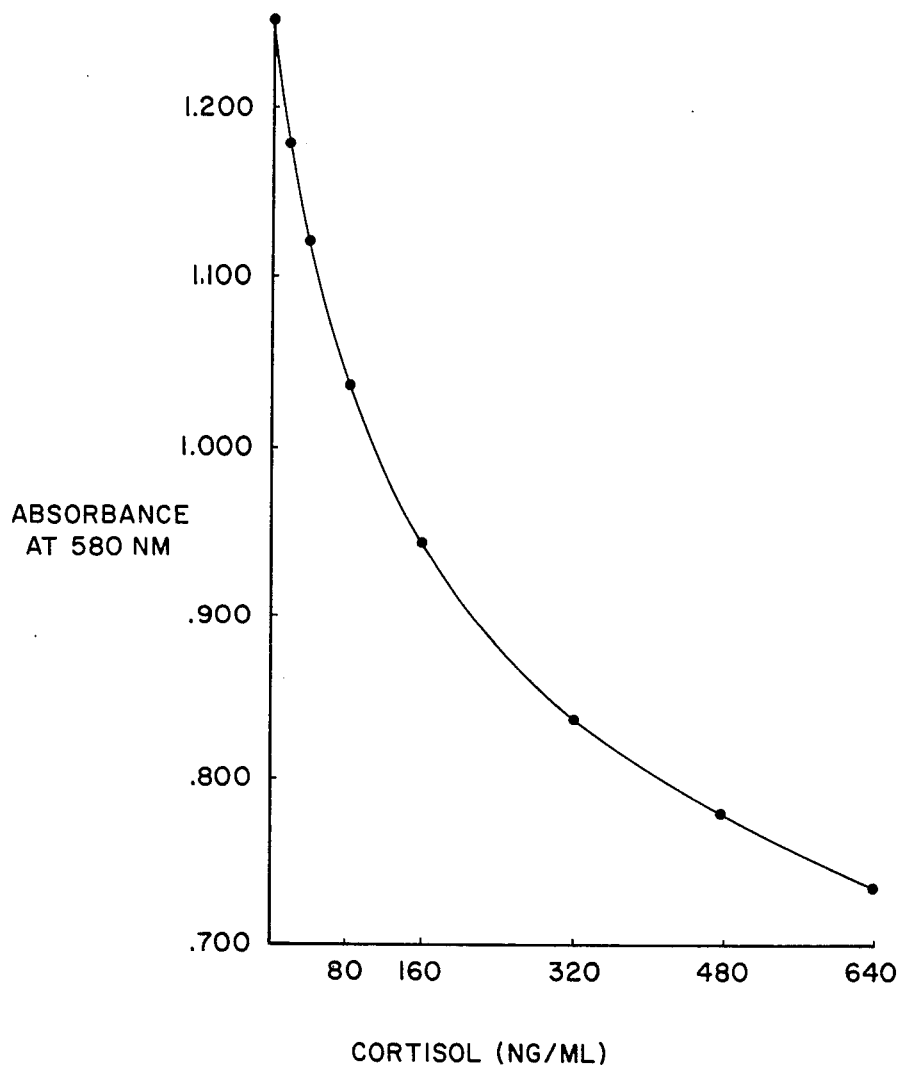
Figure 7:
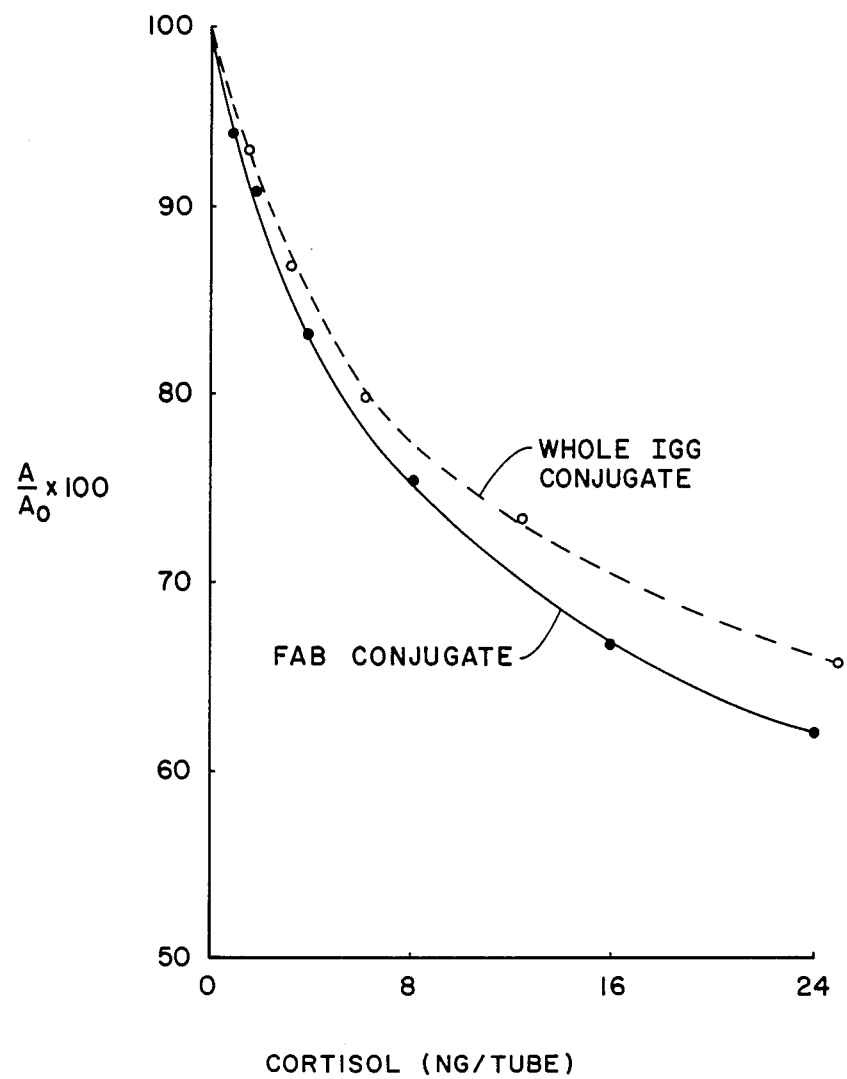

The standard curve (FIG. 6) for cortisol assay, using Fab as label, was constructed as described for IgG-cortisol conjugate (see Part VII above). The concentrations of the reagents included anti-cortisol and were the same as in Part VII. Only the concentrations of the cortisol standard were slightly different and were those reported on the horizontal axis of FIG. 6. FIG. 7 illustrates the same standard curve, showing $A/A_o \times 100$ values on the vertical axis and, in comparison, the standard curve of the IgG-cortisol conjugate (Part VII above). As can be seen, better results were obtained using the Fab label compared to a whole enzyme label.

IX. Comparison With Prior Art Method

The following additional experiments were performed for the purpose of comparing the performance characteristics of the present method with that of the prior art [Ngo and Lenhoff, *FEBS Letters* 116(2): 285(1980)-describing a homogeneous anti-enzyme labeled immunoassay based on peroxidase/anti-peroxidase interaction].

A. Inhibition of G6PDH by DNP-Anti-G6PDH Conjugate

The enzyme G6PDH (0.157 μg) was incubated at 25° C. in 0.5 ml of 0.1M Tris-HCl, pH 8, containing various concentrations of the DNP-anti-G6PDH conjugate of the present invention. After 5 minutes, 0.5 ml of substrate/indicator solution was added and the initial rate determined. The substrate/indicator solution contained NAD and G6P as in Part II-A above. In the absence of the antibody, the G6PDH gave $\Delta A = 0.649$/min. It was found that the presence of 32 μg of the DNP-anti-G6PDH in the assay mixture gave 100% inhibition of the enzyme. In contrast, as reported by Ngo and Lenhoff, the peroxidase/anti-peroxidase system gave a maximum of only 75% inhibition.

Whereas production of anti-G6PDH in rabbits capable of totally inhibiting the enzyme has been found to be normal according to the present invention (all 8 rabbits immunized with G6PDH gave anti-serum with 100% inhibitory capacity and high titer after 10 weeks), raising anti-peroxidase with high inhibitory capacity is known to be difficult. The literature reports production of anti-peroxidase that inhibits 78% and 90% maximum using rabbits and goats, respectively [Ngo and Lenhoff, ibid, and Marucci, *Immunochem.* 10: 278–280 (1972)]. In fact, the expected residual activity of the peroxidase/anti-peroxidase immune complex is used in the field of immunohistochemistry where the residual peroxidase activity is itself used as the detection signal. However, in a homogeneous anti-enzyme labeled immunoassay, such residual activity contributes to a background signal which reduces the sensitivity capabilities of the system. The present invention makes use of a enzyme/anti-enzyme system which exhibits no background to affect sensitivity.

B. Performance Characteristics of Assay for DNP-lysine

Figure 8:
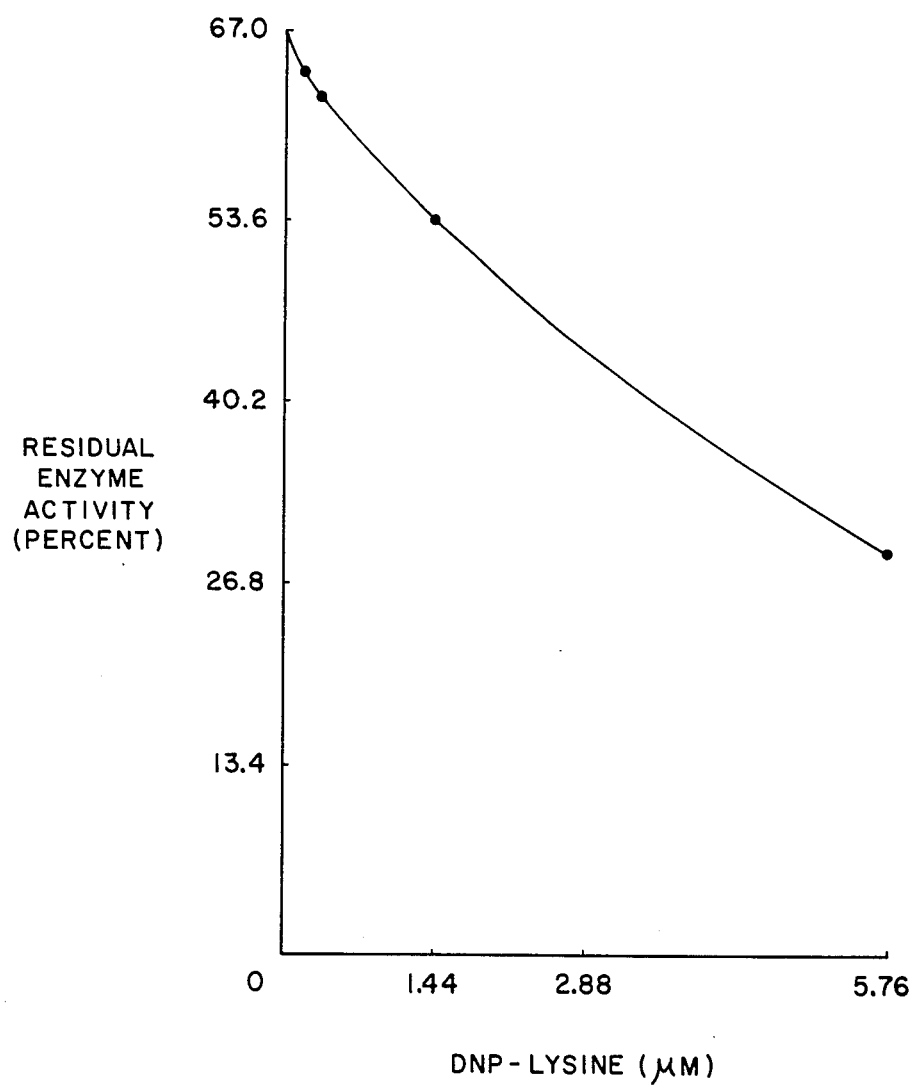

A standard curve (FIG. 8) was generated for a DNP-lysine assay following the present invention under the assay conditions of Ngo and Lenhoff, supra, i.e., a rate assay after a 5 minute incubation at 25° C. Solutions of 10 μl of various concentrations of DNP-lysine were added to 500 μl volumes of solution containing 16 μg DNP-anti-G6PDH conjugate, 100 μl anti-DNP, and 0.157 μg of G6PDH. After 5 minutes of incubation at 25° C., 0.5 ml of substrate/indicator solution was added and the initial rate determined.

Defining sensitivity as the concentration of DNP-lysine in the immunological reaction mixture which gives a 5% decrease in the response the present method in the the 25° C., 5 minute, kinetic mode showed a sensitivity of 0.36 μM. The sensitivity of the prior art peroxidase/anti-peroxidase system is calculated as no better than 2 μM, interpreting the abscissa units in FIG. 3 of the Ngo and Lenhoff reference as concentrations in the immunological reaction mixture.

From the above results, additional advantages of the present invention over the peroxidase-based method are evident. The molar ratio of anti-enzyme label to enzyme necessary to give 50% enzyme inhibition is 236 for the peroxidase-based system compared to only 35.5 for the present invention. Further, the amount of anti-enzyme label used in the DNP-lysine assay based on the prior art peroxidase system was 240 μg, whereas a significantly smaller quantity, 16 μg, was required following the present method. Additionally, it is expected that serum samples (the Ngo and Lenhoff work used pure buffer samples) will contain proteins such as hemoglobin and myoglobin, among others, having interfering peroxidative activity. However, in the present invention, the use of NAD as the cofactor for G6PDH from *L. mesenteroides* eliminates the possibility of background activity from serum G6PDH which requires NADP as cofactor. Also, as shown in the work reported above, preliminary stability studies have shown that G6PDH is stable at very low concentrations and that the substrate/indicator solution at slightly acid pH is stable for several months. In contrast, peroxidase is well known to be unstable at the low concentrations that the enzyme reagent would be stored for use in a immunoassay, and the peroxidase substrate $H_2O_2$ is not stable when mixed with appropriate chromogens and other redox indicators.

Finally, Ngo and Lenhoff do not report or suggest the possibility of using longer incubations and/or chromogens absorbing at higher wavelengths to increase the sensitivity and the practicability of the assay. By using incubation times of 60 and 20 minutes, for the immunological and enzymatic reaction respectively, and the coupled reaction of diaphorase with tetrazolium salt which allows a single reading at 580 nm (after stopping the reaction), the present method exhibited a sensitivity of 2.5 nM of biotin. The feasibility of an assay for proteins (human IgG) has also been demonstrated. A further improvement in sensitivity was obtained by using anti-G6PDH purified by affinity chromatography, reaching a sensitivity of 0.30 nM of biotin. The colorimetric method, in addition to being highly sensitive and practicable, is not affected by interferences when 50 or 100 μl of serum are incorporated in the assay. In fact, the high reading wavelength (580 nm) makes the serum color negligible. All these improvements have been used to demonstrate a practicable, homogeneous colorimetric enzyme immunoassay for cortisol in human serum (Part VII above). Further increases in sensitivity are possible, for example by detecting the enzymatic reaction with a fluorophore, such as resazurin, with an increase of sensitivity of 2–10 times over the tetrazolium salt.

Obviously, many other modifications and variations of the invention as set forth above may be made without departing from the spirit and scope hereof.

What is claimed is:

1. In a homogeneous specific binding assay method for determining an analyte in a test sample,
    wherein a reaction mixture is formed by combining said test sample with assay reagents including (a) a labeled conjugate comprising said analyte, or a binding analog thereof, coupled to a label component comprising an antibody, or fragment thereof, capable of binding to and inhibiting the catalytic activity of an enzyme, (b) a binding counterpart of said analyte, and (c) said enzyme, and
    wherein said enzymatic activity is measured in said reaction mixture as a function of the amount of said analyte in the test sample,
    the improvement which comprises employing glucose-6-phosphate dehydrogenase obtained from Leuconostoc mesenteroides (EC 1.1.1.49) as said enzyme and employing antibody to said glucose-6-phosphate dehydrogenase as said label component which inhibits said glucose-6-phosphate dehydrogenase substantially 100 percent whereby the assay method has increased sensitivity and requires the use of less labeled conjugate.

2. The method of claim 1 wherein the anti-(glucose-6-phosphate dehydrogenase) employed as said label component is an IgG antibody, or a fragment thereof, raised against glucose-6-phosphate dehydrogenase.

3. The method of claim 2 wherein said label component is a fragment of an IgG antibody.

4. The method of claim 1 wherein said analyte is selected from the group consisting of antigens and antibodies thereto; haptens and antibodies thereto; and hormones, vitamins, metabolites, and pharmacological agents, and their binding counterparts.

5. The method of claim 1 wherein said analyte is a hapten of molecular weight between about 100 and about 1500.

6. The method of claim 1 wherein said analyte is a protein or polypeptide.

7. The method of claim 1 wherein said test sample is blood or a blood refraction and said assay reagents additionally include an inhibitor for lactic dehydrogenase activity therein.

8. The method of claim 7 wherein said inhibitor is oxamic acid.

9. In a reagent system for a homogeneous specific binding assay determination of an analyte in a test sample, which system includes (1) a labeled conjugate comprising said analyte, or a binding analog thereof, coupled to a label component comprising an antibody, or fragment thereof, capable of binding to and inhibiting the catalytic activity of an enzyme, (2) a binding counterpart of said analyte, and (3) said enzyme, and which system forms with said test sample a reaction mixture in which the catalytic activity of said enzyme is a function of the amount of said analyte in said test sample,
    the improvement which comprises employing glucose-6-phosphate dehydrogenase obtained from Leuconostoc mesenteroides (EC 1.1.1.49) as said enzyme and employing antibody to said glucose-6-phosphate dehydrogenase as said label component which inhibits said glucose-6-phosphate dehydrogenase substantially 100 percent whereby the reagent system has increased sensitivity and requires less labeled conjugate.

10. The reagent system of claim 9 wherein the anti-(glucose-6-phosphate dehydrogenase) employed as said label component is an IgG antibody, or a fragment thereof, raised against glucose-6-phosphate dehydrogenase.

11. The reagent system of claim 10 wherein said label component is a fragment of an IgG antibody.

12. The reagent system of claim 9 wherein said analyte is selected from the group consisting of antigens and antibodies thereto; haptens and antibodies thereto; and hormones, vitamins, metabolites, and pharmacological agents, and their binding counterparts.

13. The reagent system of claim 9 wherein said analyte is a hapten of molecular weight between about 100 and about 1500.

14. The reagent system of claim 9 wherein said analyte is a protein or polypeptide.

15. The reagent system of claim 9 wherein said test sample is blood or a blood fraction and said system additionally includes a inhibitor for lactic dehydrogenase activity therein.

16. The reagent system of claim 15 wherein said inhibitor is oxamic acid.

17. The reagent system of claim 9 in the form of a test kit wherein said labeled conjugate, said binding counterpart, and said enzyme are in one or more containers in a packaged unit.

* * * * *

UNITED STATES PATENT AND TRADEMARK OFFICE
CERTIFICATE OF CORRECTION

PATENT NO. : 4,686,181
DATED : August 11, 1987
INVENTOR(S) : Valerio Dona'

It is certified that error appears in the above-identified patent and that said Letters Patent is hereby corrected as shown below:

On the cover page of the patent, the Assignee should be

--Miles Italiana S.p.A.,
   Brianza, Italy--.

Signed and Sealed this

Third Day of May, 1988

Attest:

DONALD J. QUIGG

Attesting Officer

Commissioner of Patents and Trademarks